United States Patent
Smith et al.

(10) Patent No.: US 7,799,327 B2
(45) Date of Patent: Sep. 21, 2010

(54) AUTOANTIBODIES UTILIZED AS CARRIER AGENTS FOR PHARMACEUTICAL COMPOUNDS USED IN CANCER TREATMENT

(76) Inventors: Henry John Smith, 2083 E. Washington Ave., San Jacinto, CA (US) 92583;
James Roger Smith, 24171 Hollyoak Apt. E, Aliso Viejo, CA (US) 92656

( * ) Notice: Subject to any disclaimer, the term of this patent is extended or adjusted under 35 U.S.C. 154(b) by 1267 days.

(21) Appl. No.: 10/745,308

(22) Filed: Dec. 24, 2003

(65) Prior Publication Data
US 2005/0147603 A1    Jul. 7, 2005

(51) Int. Cl.
*A61K 39/395* (2006.01)
*C12P 21/04* (2006.01)
*C12P 21/08* (2006.01)
*G01N 33/574* (2006.01)
*C07K 16/00* (2006.01)

(52) U.S. Cl. ............ 424/138.1; 424/142.1; 424/155.1; 424/183.1; 435/69.6; 435/70.21; 530/388.15; 530/388.21; 530/388.8

(58) Field of Classification Search ............... 424/130.1, 424/133.1, 142.1, 155.1, 181.1, 183.1; 435/69.6; 530/386
See application file for complete search history.

(56) References Cited

U.S. PATENT DOCUMENTS

| | | | |
|---|---|---|---|
| 5,780,033 A | * | 7/1998 | Torchilin et al. |
| 6,342,219 B1 | * | 1/2002 | Thorpe et al. |
| 2002/0086276 A1 | * | 7/2002 | Srivastava |

OTHER PUBLICATIONS

Goldenberg D. M. Scientific American, pp. 64-73, Mar./Apr. 1994.*
Tan E. M. Adv, Dent. Res. 10(1):44-46, Apr. 1996.*
Schwab J. et al. Clin. Exp. Immunol. 96(3):450-457, Jun. 1993.*
Kitagawa Y. et al. Journal of Immunological Methods, 96(1):7-10, 1987.*
Arbuckle M. R. et al. Scand. J. Immunol. 54:211-219, 2001.*

* cited by examiner

*Primary Examiner*—David J. Blanchard
(74) *Attorney, Agent, or Firm*—Stetina Brunda Garred & Brucker

(57) ABSTRACT

This invention describes a method whereby human autoimmune antibodies are used as carrier compounds to deliver imaging agents and pharmaceutical drugs to the tumor in the human patient. These autoantibodies have the propensity to localize in necrotic areas of tumors but not in healthy normal tissues. By combining various pharmaceutical agents with these carrier proteins it is possible to localize these agents within the necrotic areas of tumors in cancer patients. The carrier proteins may be combined with a variety of imaging agents for detection and diagnosis of tumors, and/or with a variety of radioactive or cytotoxic compounds for cancer treatment.

18 Claims, No Drawings

AUTOANTIBODIES UTILIZED AS CARRIER AGENTS FOR PHARMACEUTICAL COMPOUNDS USED IN CANCER TREATMENT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The main applications of this invention are in developing improved methods for Cancer Imaging and Cancer Treatment. One out of every four people in the US will die from cancer. There is tremendous interest in developing improved methods of cancer detection and therapy because the earlier the cancer is detected and treated the better the chances of success. Early research on targeting tumors used antibodies obtained from immunized animals. Subsequent studies have been almost exclusively devoted to developing monoclonal antibodies against tumors.

Much of the research has utilized monoclonal antibodies produced by murine hybridomas. There is however a problem when murine monoclonal antibodies are injected into cancer patients. There is a risk that the patient may develop an immune response against the "foreign" protein making further treatment ineffective. In order to avoid this problem there is intensive research into developing methods to "humanize" the monoclonal antibodies by substituting parts of the mouse antibody with human components or by developing fully human monoclonal antibodies.

This invention describes an alternative method of targeting tumors using human antibodies obtained from patients with autoimmune disease. The autoantibodies are not directed against tumor specific antigens and/or tumor associated antigens, but instead are directed against normal intracellular components that are found extracellularly within the necrotic areas often found in tumors.

Many tumors have areas of necrosis and these necrotic areas contain elevated levels of intracellular material released from dead or dying cells. This includes nuclear materials such as the nuclear membrane, nucleoproteins, DNA, histones etc. and cytoplasmic components such as mitochondria, ribosomes and soluble cytoplasmic proteins.

Patients with certain types of autoimmune disorders often produce autoantibodies directed against intracellular components. For example, patients with Systemic Lupus Erythematosus (SLE) have autoantibodies directed against nuclear antigens such as anti-deoxyribonucleoprotein (DNP) antibodies, or anti-Sm antibodies, or anti-DNA antibodies, while patients with Mixed Connective Tissue Disease (MCTD) have antibodies directed against extractable nuclear antigen (ENA). These and other autoantibodies to intracellular components can be used as "carriers" by labeling them with various imaging and therapeutic compounds. For example, antinuclear antibodies labeled with radionuclides or therapeutic drugs will bind to the expressed nuclear material found in necrotic areas of tumors. In contrast, normal healthy tissues do not have necrotic areas and will therefore not be targeted by the autoimmune antibodies.

The novelty of this invention is based on the process of using a blood product (autoantibodies) obtained from patients with autoimmune disease to develop pharmaceutical products for the detection and treatment of cancer.

This invention differs from all previous methods of using human antibodies to treat or prevent various diseases in that in those prior instances the human antibodies that were used were "protective" antibodies obtained from immunized healthy donors and used to protect the recipient from developing the same disease. For example, rhoGAM is an antibody against rhesus factor obtained from immunized donors and used to treat the pregnant mother in order to prevent rhesus disease in the fetus. Another example is the immune globulin preparation obtained from donors who had antibodies to smallpox and used prophylaticly to treat individuals who had been exposed to smallpox infection.

In contrast to the above examples, this invention describes the use of naturally occurring "pathogenic" autoantibodies obtained from individuals with one type of disease (i.e. autoimmune disease) to prepare pharmaceutical products that can be utilized to treat a completely unrelated type of disease (i.e. cancer).

A further benefit of this invention is that these are human autoantibodies and are therefore non-immunogenic to the cancer patient. They can be used repeatedly as "carriers" for cancer imaging and therapy compounds without provoking an immune response in the patient.

SUMMARY OF THE INVENTION

This invention describes the novel use of human autoimmune antibodies as carrier agents for pharmaceutical compounds used to diagnose and treat cancer. The invention describes the utilization of autoantibodies that have the capacity of binding to intracellular components released from dead or dying cells. Further, this invention describes the process whereby these autoantibodies can be obtained from patients with autoimmune disease and used as "carrier" compounds by labeling them with various imaging agents and therapeutic drugs. The labeled carrier compounds have the propensity of binding to substances found in areas of necrosis such as those found in tumors. By combining various imaging agents or drugs to these carrier proteins it is possible to utilize the labeled carrier proteins to detect and treat tumors in cancer patients.

The autoantibodies that can be used as carrier proteins are exemplified by the anti-nuclear antibodies seen in patients with SLE. These anti-nuclear antibodies can be used as carrier proteins for cancer imaging or anti-cancer drug treatment in cancer patients. Anti-nuclear antibodies labeled with the tumor imaging and/or anti-cancer drug will localize in necrotic areas found in tumors but will not localize in healthy tissues that do not have areas of necrosis.

The autoantibodies described here are fully human derived and are therefore non-immunogenic to the cancer patient. They can be used repeatedly as "carriers" for cancer imaging and therapy compounds without provoking an immune response in the patient.

DESCRIPTION OF THE INVENTION

This invention describes a method for improved delivery of diagnostic and pharmaceutical agents to tumors using human autoimmune antibodies as "carriers" for compounds used to diagnose and/or treat tumors.

This invention is based on the observation that these autoantibodies have a propensity for binding to certain intracellular material found extracellularly within necrotic areas in tumors but not in healthy tissues. The invention describes the process whereby various diagnostic and therapeutic agents are combined with these autoantibodies and used in the detection and treatment of cancer.

A major benefit of this invention is that these are fully human derived antibodies and therefore cancer patients can receive repeated treatment without developing an immune reaction to the carrier antibody.

There are a variety of autoantibodies that may be used as carrier proteins. These include autoantibodies directed against intracellular components of the cell such as antinuclear antibodies, anti-RNP antibodies, anti-Sm antibodies, anti-DNA antibodies, anti-ENA antibodies, anti-mitochondrial antibodies, anti-Golgi antibodies and antibodies to other cytoplasmic proteins. The autoantibodies may be of the IgG class and/or the IgM class and/or the IgA class of immunoglobulin. In the preferred embodiment of this invention antinuclear antibodies obtained from lupus patients are described. However, other autoimmune antibodies directed against a variety of intracellular components of the cell may be similarly employed and are considered within the scope of this invention.

Antinuclear antibodies are commonly found in patients with SLE or other autoimmune diseases. Blood from the SLE patient is collected and allowed to clot. The serum containing the autoantibody of interest is fractionated by standard laboratory techniques in order to concentrate and purify the autoantibodies. These procedures are known to those skilled in the art. For example, one purification process is to concentrate the immunoglobulin fraction using ammonium salt precipitation and gel-filtration; followed by affinity chromatography to isolate the desired autoantibodies. For example, the immunoglobulin fraction in serum is precipitated by adding saturated ammonium sulphate solution to reach a final concentration of 33% saturation; the precipitated immunoglobulin fraction is dissolved in phosphate buffer solution and dialysed against the buffer to remove any remaining ammonium sulphate. The antinuclear antibodies in the immunoglobulin fraction are then isolated using affinity chromatography or affinity binding techniques.

In the preferred embodiment of the invention the blood of the patient with autoimmune disease is processed using a technique called apheresis. Apheresis is a procedure which utilizes an extracorporeal device to remove selected blood components, such as the IgG fraction, from the patient's blood and returns the cleaned blood to the patient. The IgG fraction containing the autoantibodies of interest is then treated to purify the antibodies using standard laboratory procedures such as affinity chromatography or affinity binding techniques.

Antigen Preparation.

There are two basic procedures that can be used:

One method utilizes fixed whole isolated nuclei as the binding ligand. The nuclei can be obtained from many different human and animal sources. In the preferred embodiment of this invention nuclei obtained from human cells are used. For example, tissue culture human cell lines such as Hela or Hep 2 can be used; or buffy coat cells obtained from human blood. The cells are suspended in an osmotically balanced sucrose solution and disrupted using a mechanical homogenizer. Intact cells and large particulate debris are sedimented using low speed centrifigation and discarded. The supernatent is then centrifuged at a higher speed to sediment the isolated nuclei. The isolated nuclei are resuspended in a low volume of buffer and fixed by adding ethyl alcohol or glutaldehyde. After fixation the nuclei are washed several times in phosphate buffer to remove any remaining fixing agent.

Alternatively, a nuclear material extract obtained from human or animal sources can be used. In the preferred embodiment of this invention the nuclear extract is prepared from nuclei obtained from human cells. For example, tissue culture human cell lines such as Hela or Hep 2 can be used; or buffy coat cells obtained from human blood. To prepare the nuclear extract the cells are suspended in an osmotically balanced sucrose solution and disrupted using a mechanical homogenizer. Intact cells and large particulate debris are sedimented using low speed centrifigation and discarded. The superntatent is then centrifuged at a higher speed to sediment the isolated nuclei. The isolated nuclei are resuspended in buffer and disrupted using a mechanical homogenisor or repeated freeze thaw cycles. The nuclear extract is then used to prepare an affinity column. The nuclear extract is fixed to an insoluble support such as agarose or sepharose beads using cyanogen bromide treatment or other means of attachment.

The above examples are provided for illustration only. There are many other purification methods known to those skilled in the art that may be employed without affecting the novelty of this invention.

Antibody Preparation

Blood or blood products from individuals with autoimmune disease is available from blood donation or from commercial sources. There are various procedures for blood donation. Either whole blood is donated, or a procedure termed "plasmapheresis" is used in which a specified volume of the donor's blood is processed through a cell separator machine that removes the plasma and returns the blood cells to the patient. There is also a process termed "apheresis" in which the donor's blood is continuously processed through a machine that removes the immunoglobulin fraction from the blood, and returns the other components of the blood to the patient. The immunoglobulin fraction includes the pathogenic autoantibodies that are involved in the disease process, and therefore their removal may ameliorate the symptoms of the disease. Apheresis has been used to treat a number of autoimmune diseases including myasthenia gravis, multiple sclerosis, rheumatoid arthritis and systemic lupus erythematosus (SLE). The autoantibodies of interest are then purified using standard laboratory procedures such as affinity chromatography or affinity binding techniques.

In the preferred embodiment of the invention the patient with SLE is connected to the apheresis machine and the blood is circulated over an affinity chromatography column. The affinity column is typically composed of either Protein A or anti-human immunoglobin antibody that is bound to an insoluble support such as agarose or sepharose, and contained in a cartridge. The affinity column binds out the immunoglobulin fraction of the blood allowing the other blood components to return to the patient. The treatment is performed over a period of several hours that allows most of the immunoglobin fraction to be removed. Further removal of the immunoglobulin fraction is accomplished by repeating the treatment on a daily or periodic basis over a period of time. Patients generally obtain relief from the disease although symptoms may return as new autoantibodies are formed. The IgG fraction bound to the affinity column is eluted off the column and the autoantibodies are purified using standard laboratory procedures such as affinity chromatography or affinity binding techniques There are several types of apheresis equipment available. One process uses a single use disposable cartridge containing protein-A linked to silica (e.g., a PROSORBA column). There is also a procedure that extends the life of a cartridge containing protein-A linked to sepharose (the e.g., an IMMUNOSORBA column) by utilizing a computerized automated process that alternates binding and elution of the immunoglobulin fraction. The autoantibodies in the eluate are purified using standard laboratory procedures such as affinity chromatography or affinity binding techniques.

In the preferred embodiment of the invention a process whereby only the pathogenic autoantibodies of interest are removed by apheresis in a single process is described. To accomplish this an affinity column is prepared in which the autoantigen is prepared as described earlier (see antigen preparation). The patient's blood is continuously passed through the affinity cartridge which binds out only the autoantibodies of interest leaving the other blood components to be returned to the patient. The bound autoantibodies are then eluted off the affinity column using a suitable elution buffer resulting in a purified autoantibody preparation.

Other methods of obtaining large quantities of autoantibodies include using fully human hybridomas in which antibody producing autoimmune cells from patients with autoimmune disease such as SLE are fused with a human cell line to produce monoclonal autoimmune antibodies. Another method utilizes transgenic animals in which the animal's immune system is replaced with antibody producing cells from a human source. By transferring immune cells from a patient with autoimmune disease into the transgenic animal it can be induced to produce fully human autoantibodies.

The various methods of obtaining autoimmune antibodies from patients either by blood donation, or plasmapheresis, or apheresis or other means are known to those skilled in the art and are considered to be within the scope of this invention.

The immunoglobulin fraction containing the autoantibodies is fractionated by standard laboratory techniques in order to concentrate and purify the autoantibodies. These procedures are known to those skilled in the art. One purification process is to use affinity chromatography or affinity binding to isolate the desired autoantibodies as described earlier. For example, an affinity column is prepared and the immunoglobulin fraction is allowed to pass through the column. Any antinuclear antibodies present will bind to the fixed nuclei or nuclear extract while unbound material will pass through. The bound antibodies are then eluted off the column using a low pH glycine/HCl buffer or other suitable eluting agent. The affinity purified antibodies are neutralized using an alkaline solution such as NaOH and diluted in a neutral buffer such as phosphate buffered saline. To minimize denaturation the whole procedure is performed in the cold.

The above examples are provided for illustration only. There are many other purification methods known to those skilled in the art that may be employed without affecting the novelty of this invention.

In certain situations it may be preferable to use the binding fragments Fab or F(ab')$_2$ of the antibody molecule as the carrier protein and this also falls within the scope of this invention. In this context, the terms "autoimmune antibodies" and "autoantibodies" refer to either the whole intact IgG or IgM antibody molecule or to the binding fragments of the antibody molecule.

The purified autoantibodies are then combined with a variety of pharmaceutical compounds and used for tumor imaging and cancer treatment.

Tumor Imaging

The purified autoantibodies can be combined with a wide variety of tumor imaging agents:

For tumor imaging studies there are a variety of radionuclides including Tc-99m, I-123, I-125, In-111, In-113m, Ga-67, or other gamma-emitters. The carrier protein can be iodinated using the chloramine-T method to label the protein with I-125 or I-131. Other radionuclides may be attached to the carrier autoantibody by chelation with benzyl EDTA or DPTA conjugation procedures. These procedures are known to those skilled in the art and are considered within the scope of this invention. The radionuclide labeled carrier autoantibodies are then injected into the cancer patient where they will come into contact with the tumor tissue. Many tumors contain areas of necrosis composed of dead and dying cells that have released their intracellular contents into the surrounding environment. The labeled antinuclear antibodies will bind to the expressed intracellular material and the radioactivity will become localized within the necrotic areas of the tumor. In contrast, normal tissues contain healthy intact cells and the labeled autoantibodies cannot react with the protected intracellular components within healthy cells. There will be much less radioactivity bound within healthy tissue as compared to tumor tissue. The quantity of radioactivity in different tissue locations is measured using gamma ray scanning or tissue sampling techniques. As even small tumors contain areas of necrosis this method may be useful in detecting early tumors.

Another method of tumor detection using this invention is to combine the carrier autoantibodies with a radiopaque compound such as barium compounds, gallium compounds, and thallium compounds. The methods of combining autoantibodies to these compounds are known to those skilled in the art and are considered within the scope of this invention. When injected into the cancer patient the radiopaque labeled autoantibodies will localize within the necrotic areas of the tumor and are detected by X-radiography.

Another method of tumor detection employs magnetic resonance technology using magnetic resonance-enhancing compounds such as gadolinium, copper, iron, and chromium. The methods of combining autoantibodies to these compounds are known to those skilled in the art and are considered within the scope of this invention. When injected into the cancer patient the autoantibodies labeled with the magnetic resonance-enhancing compounds will localize within the necrotic areas of the tumor and are detected by magnetic resonance imaging equipment.

Cancer Treatment

The purified autoantibodies can be combined with a wide variety of radionuclides and cytotoxic drugs. These can be broadly classified into the following groups.

The radiologic group includes alpha-emitting and beta-emitting radionuclides such as I-131, Yt-99, Cu-67, Au-198, P-32, and other cytotoxic radionuclides. The radionuclides can be conjugated to the carrier autoantibody using methods that are familiar to those skilled in the art. For example, the carrier protein can be iodinated using the chloramine-T method to label the protein with I-125 or I-131. Other radionuclides may be attached to the carrier autoantibody by chelation with benzyl EDTA or DPTA conjugation procedures. For cancer treatment a high dosage of radioactivity is employed. The labeled carrier protein is then injected into the cancer patient where it will localize in the necrotic regions within the tumor. From there the radiation will penetrate into the surrounding tumor where it will have a cytotoxic effect upon the tumor cells.

The cytotoxic drug group includes the folate inhibitors, pyrimidine analogs, purine analogs, alkylating agents and antibiotics. Specific examples include acivicin, aclarubicin, acodazole, adriamycin, ametantrone, aminoglutethimide, anthramycin, asparaginase, azacitidine, azetepa, bisantrene, bleomycin, busulfan, cactinomycin, calusterone, caracemide, carboplatin, carmustine, carubicin, chlorambucil, cisplatin, cyclophosphamide, cytarabine, dacarbazine, dactinomycin, daunorubicin, dezaguanine, diaziquone, doxorubicin, epipropidine, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin. Also included are the toxins such as ricin and diptheria toxin.

All these compounds can be conjugated to the carrier autoantibody using methods that are familiar to those skilled in the art. For example, many carboxylic acid-containing compounds such as methotrexate can be conjugated to immunoglobulins through an active ester intermediate by reacting the compound with N-hydroxysuccinimide and dicyclohexylcarbodiimide; amino sugar containing drugs such as adriamycin and daunomycin may be covalently bound to antibodies by periodate oxidation of the drug, followed by linking of the oxidized drug to the immunoglobulin and subsequent reduction of the product with sodium borohydride. The methods of conjugating any particular drug to the carrier protein will vary depending upon the nature of the drug. However, these are performed according to conventional laboratory methods and are considered to be within the scope of this invention. The labeled carrier protein is then injected into the cancer patient where it will localize in the necrotic regions within the tumor. From there the drug will diffuse into the surrounding tissues where it will have a cytotoxic effect upon the tumor cells.

The biological response modifier group includes cytokines such as tumor necrosis factor, interferons, angiostatin and immune stimulators such as animal or microbial proteins. These compounds can be conjugated to the carrier autoantibody using methods that are familiar to those skilled in the art. For example, glutaraldehyde may be used to cross-link the free amino groups of the antibody and modifier protein. Other methods may be employed using conventional laboratory procedures and are considered to be within the scope of this invention. The labeled carrier protein is then injected into the cancer patient where it will localize in the necrotic regions within the tumor and have the maximum effect upon the surrounding tissue. The effect may be to stimulate an inflammatory response as in the case of tumor necrosis factor, or to inhibit the growth of new blood vessels to the tumor as in the case of angiostatin, or to stimulate an immune response within the tumor by the presence of a foreign animal or microbial protein.

Non-Immunogenicity of the Carrier Protein

The carrier autoantibodies are obtained from a human source and being fully human in composition they are non-immunogenic to the human cancer patient. They can therefore be used repeatedly for tumor imaging and for cancer treatment over a prolonged period of time without provoking an adverse immune response from the patient.

What is claimed is:

1. A method of treating cancer in a patient comprising administering pathogenic human autoimmune antibodies obtained from patients having an autoimmune disease distinct from cancer as carrier agents for therapeutic pharmaceuticals, wherein the human autoimmune antibodies, and/or binding fragments Fab and $F(ab')_2$ of the human autoimmune antibodies have the capacity to bind to intracellular components of the cell that are located extracellularly within necrotic areas of tumors, and wherein the human autoimmune antibodies, and/or binding fragments Fab and $F(ab')_2$ of the human autoimmune antibodies are not directed to tumor-specific antigens and/or tumor-associated antigens.

2. The method according to claim 1 wherein the human autoimmune antibodies and/or binding fragments Fab and $F(ab')_2$, of the human autoimmune antibodies are selected from the group consisting of anti-RNP antibodies, anti-Sm antibodies, anti-DNA antibodies, anti-ENA antibodies, anti-mitochondrial antibodies, and anti-Golgi antibodies.

3. The method according to claim 1 wherein the human autoimmune antibodies used as carrier agents are obtained from patients with autoimmune disease by means selected from the group consisting of blood donation, plasmapheresis, apheresis, using human hybridomas and using transgenic animals.

4. The method according to claim 3 wherein the human autoimmune antibodies used as carrier agents are obtained in a purified form by using apheresis and employing an affinity column that selectively binds the pathogenic antibodies of interest.

5. The method according to claim 1 wherein the use of the human autoimmune antibodies, and/or the binding fragments of the antibody, as carrier agents for cancer treatment compounds can be repeated without eliciting a host immune response in the cancer patient.

6. The method according to claim 1 further comprising the step of utilizing a therapeutic dosage of a variety of radionuclides linked to the human autoimmune antibodies and injected into the cancer patient.

7. The method according to claim 1 further comprising the step of utilizing a therapeutic dosage of a variety of cytotoxic anti-cancer drugs linked to the human autoimmune antibodies and injected into the cancer patient.

8. The method according to claim 1 further comprising the step of utilizing a variety of biological response modifiers linked to the human autoimmune antibodies and injected into the cancer patient.

9. The method according to claim 1 further comprising the step of utilizing a variety of toxins linked to the human autoimmune antibodies and injected into the cancer patient.

10. The method according to claim 1 further comprising the step of utilizing a variety of foreign animal or microbial protein linked to the human autoimmune antibodies and injected into the cancer patient.

11. The method according to claim 1 further comprising the step of utilizing a variety of blood vessel growth inhibiting compounds linked to the human autoimmune antibodies and injected into the cancer patient.

12. The method according to claim 2 further comprising the step of utilizing a therapeutic dosage of a variety of radionuclides linked to the human autoimmune antibodies and injected into the cancer patient.

13. The method according to claim 2 further comprising the step of utilizing a therapeutic dosage of a variety of cytotoxic anti-cancer drugs linked to the human autoimmune antibodies and injected into the cancer patient.

14. The method according to claim 2 further comprising the step of utilizing a variety of biological response modifiers linked to the human autoimmune antibodies and injected into the cancer patient.

15. The method according to claim 2 further comprising the step of utilizing a variety of toxins linked to the human autoimmune antibodies and injected into the cancer patient.

16. The method according to claim 2 further comprising the step of utilizing a variety of foreign animal or microbial protein linked to the human autoimmune antibodies and injected into the cancer patient.

17. The method according to claim 2 further comprising the step of utilizing a variety of blood vessel growth inhibiting compounds linked to the human autoimmune antibodies and injected into the cancer patient.

18. The method according to claim 1 wherein the autoimmune disease is either Systemic Lupus Erythematosus or Mixed Connective Tissue Disease.

* * * * *